United States Patent
Zhang et al.

(10) Patent No.: US 8,247,780 B2
(45) Date of Patent: Aug. 21, 2012

(54) HIGH DENSITY, PROPORTIONAL-MODE, APD ARRAYS FOR INDIVIDUAL SCINTILLATOR READOUT IN PET APPLICATIONS

(75) Inventors: Nan Zhang, Knoxville, TN (US); Ronald Grazioso, Knoxville, TN (US); Debora Henseler, Erlangen (DE); Matthias J. Schmand, Lenoir City, TN (US)

(73) Assignees: Siemens Aktiengesellschaft, Munich (DE); Siemens Medical Solutions USA, Inc., Malvern, PA (US)

( * ) Notice: Subject to any disclaimer, the term of this patent is extended or adjusted under 35 U.S.C. 154(b) by 91 days.

(21) Appl. No.: 12/943,164

(22) Filed: Nov. 10, 2010

(65) Prior Publication Data

US 2012/0112083 A1 May 10, 2012

(51) Int. Cl.
*G01T 1/20* (2006.01)
(52) U.S. Cl. .................................. 250/370.11
(58) Field of Classification Search ........ 250/370.01–370.15; 378/98.8
See application file for complete search history.

(56) References Cited

U.S. PATENT DOCUMENTS

| 7,535,011 B2 | 5/2009 | Chowdury et al. |
| 2003/0105397 A1 | 6/2003 | Tumer et al. |
| 2011/0215248 A1* | 9/2011 | Lewellen et al. ........ 250/363.03 |

FOREIGN PATENT DOCUMENTS

WO  2008121072 A1  10/2008

OTHER PUBLICATIONS

Kataoka et al., "Development of an APD-based PET module and preliminary resolution performance of an experimental prototype gantry," 2010, IEEE Transactions on Nuclear Science, vol. 57, No. 5, pp. 2448-2454.*
Hiraide et al., "Development of a low-noise front-end electronics for a multi-channel APD readout system," 2005, IEEE Nuclear Science Symposium Conference Record, pp. 580-583.*

* cited by examiner

*Primary Examiner* — Kiho Kim
(74) *Attorney, Agent, or Firm* — Peter Kendall

(57) ABSTRACT

The present invention is a photodetector including improved photosensors configured of an array of small (sub-millimeter) high-density avalanche photodiode cells utilized to readout a single scintillator. Each photosensor comprises a plurality of avalanche photodiodes cells arranged in an (n×n) array of avalanche photodiode cells (where, n>1) that are coupled to a single scintillation crystal. The overall (n×n) array area as the photosensor is the same as the area of a face of the scintillator and each avalanche photodiode cell has a surface area that is not greater than one square millimeter. The photosensor is also configured to facilitate reading the output of each avalanche photodiode cell in the array. By reading out each small avalanche photodiode cell independently, the noise and capacitance are minimized and thereby provide a more accurate determination of energy and timing.

20 Claims, 4 Drawing Sheets

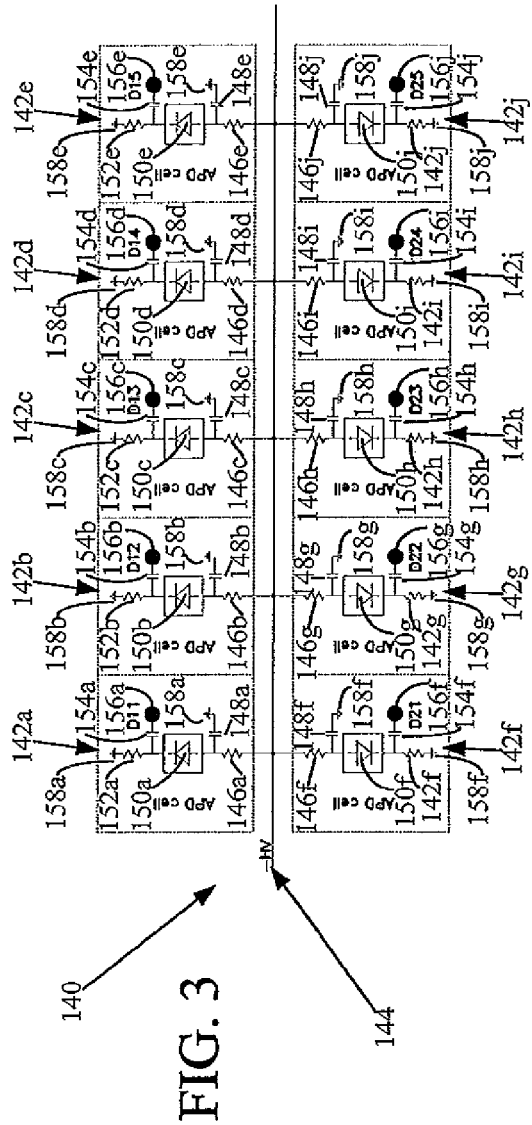
FIG. 3
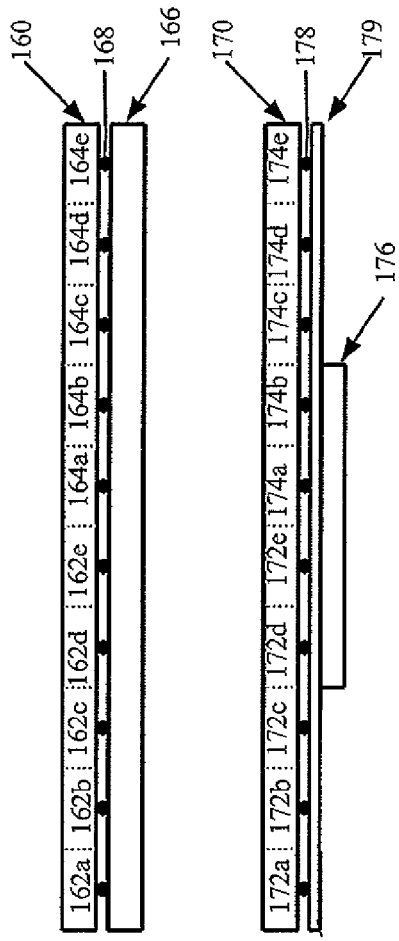
FIG. 4A
FIG. 4B

HIGH DENSITY, PROPORTIONAL-MODE, APD ARRAYS FOR INDIVIDUAL SCINTILLATOR READOUT IN PET APPLICATIONS

BACKGROUND OF THE INVENTION

I. Field of the Invention

The present invention relates to medical imaging systems; more particularly, the present invention relates to a high density, highly integrated, APD photosensor (Avalanche Photodiode) array for scintillation crystal readout in detectors utilized in imaging systems using positron emission tomography (PET).

II. Background Information

Nuclear medicine is a unique medical specialty wherein radiation is used to acquire images, which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions, which emanate from the body and are captured by a scintillation crystal, with which the photons interact to produce flashes of light or "events." Events are detected by an array of photo detectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce images for diagnosing the biochemistry or physiology of a specific organ, tumor or other metabolically active site. Measurement of the tissue concentration of a positron emitting radionuclide is based on coincidence detection of the two gamma photons arising from positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence event, they also identify a line of response, or LOR, along which the annihilation event has occurred.

An example of a PET method and apparatus is described in U.S. Pat. No. 6,858,847, which patent is incorporated herein by reference in its entirety. After being sorted into parallel projections, the LORs defined by the coincidence events are used to reconstruct a three-dimensional distribution of the positron-emitting radionuclide within the patient. PET is particularly useful in obtaining images that reveal bioprocesses, e.g. the functioning of bodily organs such as the heart, brain, lungs, etc. and bodily tissues and structures such as the circulatory system.

In order to minimize patient exposure to radiation, detectors utilized in PET imaging systems must be able to detect low levels of incident optical photons or ionizing particles. In such imaging devices it is often advantageous to employ radiation detection devices having internal gain; avalanche photodiodes (APDs) are commonly used in such devices to provide the desired detection sensitivity. An APD is a semiconductor device that is biased near the breakdown region such that charge generated as a result of the absorption of an incident photon is amplified in the APD itself as a result of a cascading effect as charge is accelerated by the high bias potential applied across the p-n junction of the device. In such imaging devices, it is desirable that the APD exhibit low noise and high gain. Certain devices, such as medical imagers (e.g., using gamma radiation), also require relatively large arrays (e.g., about 5 cm.sup.2 or larger) of high quality, low noise APDs.

One detector configuration in PET imaging systems utilizing APD arrays is configured in a one-to-one coupling configuration, where one APD is coupled to one scintillation crystal. To collect the maximum amount of light from the scintillator, the APD has to have the same surface area as the scintillator crystal to which it is coupled. This can result in large surface area APDs, which increases the APD noise and capacitance. The noise and capacitance of an APD is directly proportional to its surface area. As the noise and capacitance of the APD increases, its capacity to accurately determine the proper energy and timing of an event decreases. This results in poor PET detector performance and is a main reason why APDs are not commonly used as photosensors in detectors in PET imaging systems. There is a need for a photosensor array configuration that can take advantage of the high gain resulting from the use of APDs in the array while simultaneously reducing the noise and capacitance resulting from increasing the size of APDs when used in photosensors.

One detector which utilizes the concept of a high density photosensor readout coupled to a single scintillator is the SiPM (Silicon Photomultiplier). A SiPM uses a very dense array of Geiger-mode APDs which are typically resistively connected in parallel to provide a single readout channel. A significant drawback of this type of this type of detector is that each of the SiPM APD cells is nonlinear since they operate in Geiger mode. Detectors utilizing SiPM Geiger mode APDs in each cell operate in binary mode. Accordingly, the respective output of SiPM APD cells can only be zero or one. This is a fundamental problem, because each SiPM APD cell is only capable of counting one photon and cannot indicate that more than one photon has been received. For example, if two photons reach the same SiPM APD cell at the same approximate time, there is no way of knowing that two photons have been received by the SiPM APD cell. To increase the linearity of a SiPM, the SiPM cell density must be increased. However, increasing the cell density of a SiPM causes a decrease in the fill factor of the device. For most SiPM devices, there is a trade-off between linearity and fill factor. There is a need for a configuration of APD arrays that overcomes this limitation wherein an array of APD cells operate in proportional mode and are linear.

Some developers in the industry have investigated operating SiPMs below the breakdown voltage in proportional mode for CT imaging to overcome the inherent nonlinearity of the device. However, the proposed detector still uses a common readout of the summed SiPM cells. There is a need for a system that facilitates individual cell readout of the cells comprising an APD array.

SUMMARY OF THE INVENTION

Consistent with embodiments of the present invention, the present invention comprises an improved photodetector including improved photosensors configured as an array of small (sub-millimeter) high-density avalanche photodiode cells utilized to readout a single scintillator. Each photosensor comprises a plurality of avalanche photodiode cells arranged in an (n×n) array (where, n>1) that are coupled to a single scintillation crystal. The overall (n×n) array area of the photosensor is substantially the same as the area of a face of the scintillator and each avalanche photodiode cell has a surface area that is not greater than one square millimeter. The photosensor array is also configured with circuitry to facilitate reading the output of each avalanche photodiode cell in the array separately.

It is to be understood that both the foregoing summary of the invention and the following detailed description are exemplary and explanatory only, and should not be considered restrictive of the scope of the invention, as described and claimed. Further, features and/or variations may be provided in addition to those set forth herein

BRIEF DESCRIPTION OF THE DRAWINGS

The accompanying drawings, which are incorporated in and constitute a part of this disclosure, illustrate various embodiments and aspects of the present invention. In the drawings:

FIG. 3 is a schematic example of an embodiment of the biasing circuit and the signal output connection of the APD array illustrated in FIG. 2b in one embodiment of the present invention;

FIG. 4a is a side view of a package configuration of a sub-millimeter APD array connected to a frond end APD-ASIC in one embodiment of the present invention;

FIG. 4b is a side view of a package configuration of a sub-millimeter APD array connected to a frond end APD-ASIC in a second embodiment of the present invention illustrating a smaller ASIC die;

GENERAL DESCRIPTION

Figure 1A:
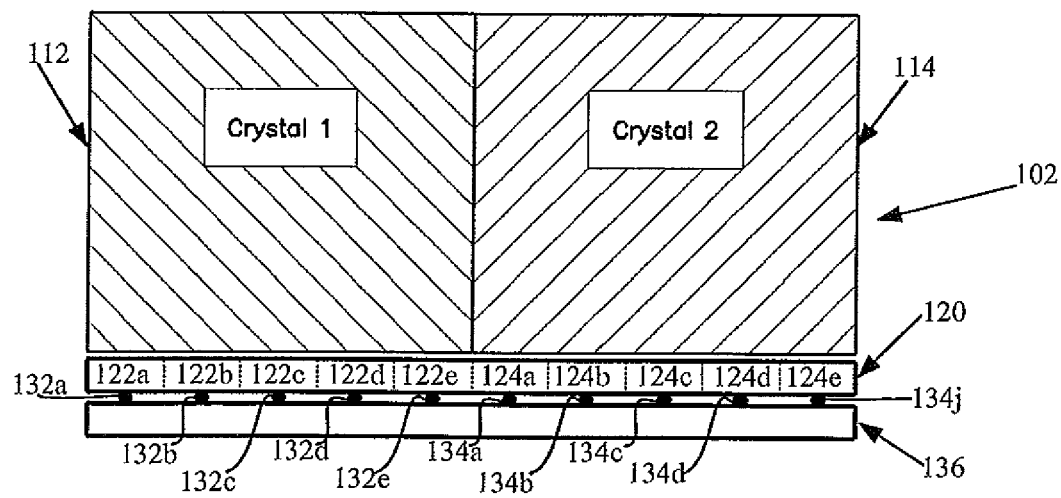
FIG. 1a is a side view of a sub-millimeter 2×2 APD array coupled to a single scintillator crystal in one embodiment of the present invention.

Consistent with embodiments, the present invention is an improved photodetector configured for use in PET imaging systems, wherein the improved photodetector shall include at least one scintillator crystal and an APD photosensor array coupled to the at least one scintillator crystal. The APD photosensor array is sized so that its surface area is substantially equivalent to a surface area of a face of the scintillator crystal. The APD photosensor array comprises a plurality of avalanche photodiodes arranged in an n×n array of cells that include support circuitry. Each APD cell has a separate output for the avalanche photodiode positioned thereon so that each avalanche photodiode can be read independently. Each APD cell is defined as sub-millimeter because the surface area of each APD cell is <1.0 mm×<1.0 mm. In one embodiment, the surface area of each APD cell shall be 0.05 mm 1.0 mm×0.05 mm-1.0 mm. By reading the output from each small sub-millimeter APD cell independently, the noise and capacitance are minimized and thereby provide a more accurate determination of energy and timing.

DETAILED DESCRIPTION

The following detailed description refers to the accompanying drawings. Wherever possible, the same reference numbers are used in the drawings and the following description to refer to the same or similar parts. While several embodiments and features of the invention are described herein, modifications, adaptations and other implementations are possible, without departing from the spirit and scope of the invention. Rather these embodiments are provided so that this disclosure will be complete and will fully convey the invention to those skilled in the art. For example, substitutions, additions or modifications may be made to the components illustrated in the drawings, and the methods described herein may be modified by substituting, reordering or adding steps to the disclosed methods. Accordingly, the following detailed description does not limit the invention. Instead, the proper scope of the invention is defined by the appended claims.

Figure 1B:
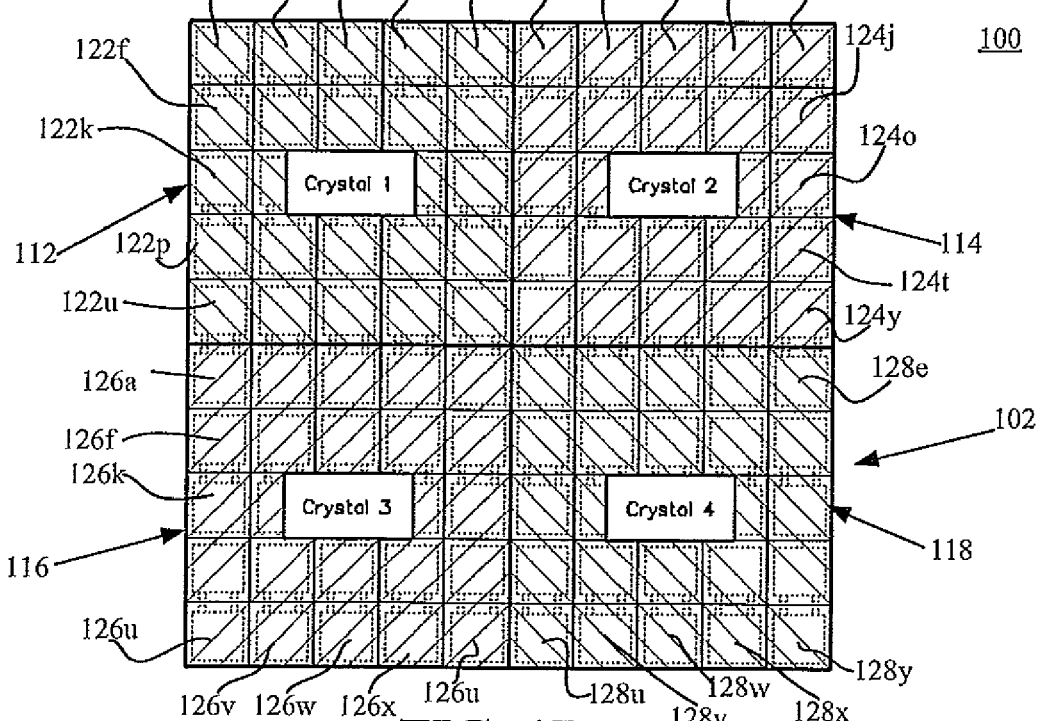
FIG. 1b is a top view of a sub-millimeter 2×2 APD array coupled to a single scintillator crystal in one embodiment of the present invention.

The present invention comprises the use of a high density, highly integrated APD (Avalanche Photodiode) array to readout one or more scintillation crystals within a photo detector used in PET imaging applications. One embodiment of the invention, shown in FIGS. 1A and 1B, illustrate a block detector 100, utilizing a high density, highly integrated APD array 120 to read each scintillation crystal 112, 114, 116, 118 within an array of scintillation crystals 102.

Unlike a typical detector in PET imaging systems that utilize a one-to-one crystal to photosensor configuration, or a block detector where the number of photosensors is less than the number of crystals in the configuration, the detector embodied in the present invention utilizes a configuration in which the number of photosensors, APDs, is always greater than number of crystals. In the example embodiment illustrated in FIGS. 1A and 1B, there are twenty-five photo sensors to each scintillation crystal. In the embodiment illustrated, a two by two array of scintillation crystals 102 is coupled to a ten by ten array of photo sensor cells 120, wherein each cell includes an APD. As illustrated, each scintillation crystal 112, 114, 116, 118 is coupled to a five by five array of APD photo sensor cells positioned to read out each scintillation crystal 112, 114, 116, 118 separately. As illustrated in FIG. 1B, crystal one 112 is coupled to a first array of APD photo sensors 122a-122y; crystal two 114 is coupled a second array of APD photo sensors 124a-124y; crystal three 116 is coupled to a third array of APD photo sensors 126a-126y; and crystal four 118 is coupled to a fourth array of APD photo sensors 128a-128y. As illustrated in FIG. 1B, the combination of scintillation crystals one 112, two 114, three 116 and four 118 into a array shows that that photo detectors 100 of the type generated using the present invention may be a subset of a larger array detector.

Each APD in the APD array 120 reading light from the block of scintillation crystals 112, 114, 116 and 118 are read out independently through ball grid array (BGA) connections to a highly integrated ASIC 136 to provide accurate energy and timing information. FIG. 1A illustrates the BGA 132a-132e connecting APD cells 122a-122e to ASIC 136 and the BGA 134a-134e connecting APD cells 124a-124e to ASIC 136. (Similar BGA connecting the remaining APD cells to ASIC 136 exists but are not shown in FIG. 1A).

Figures 2A, 2B:
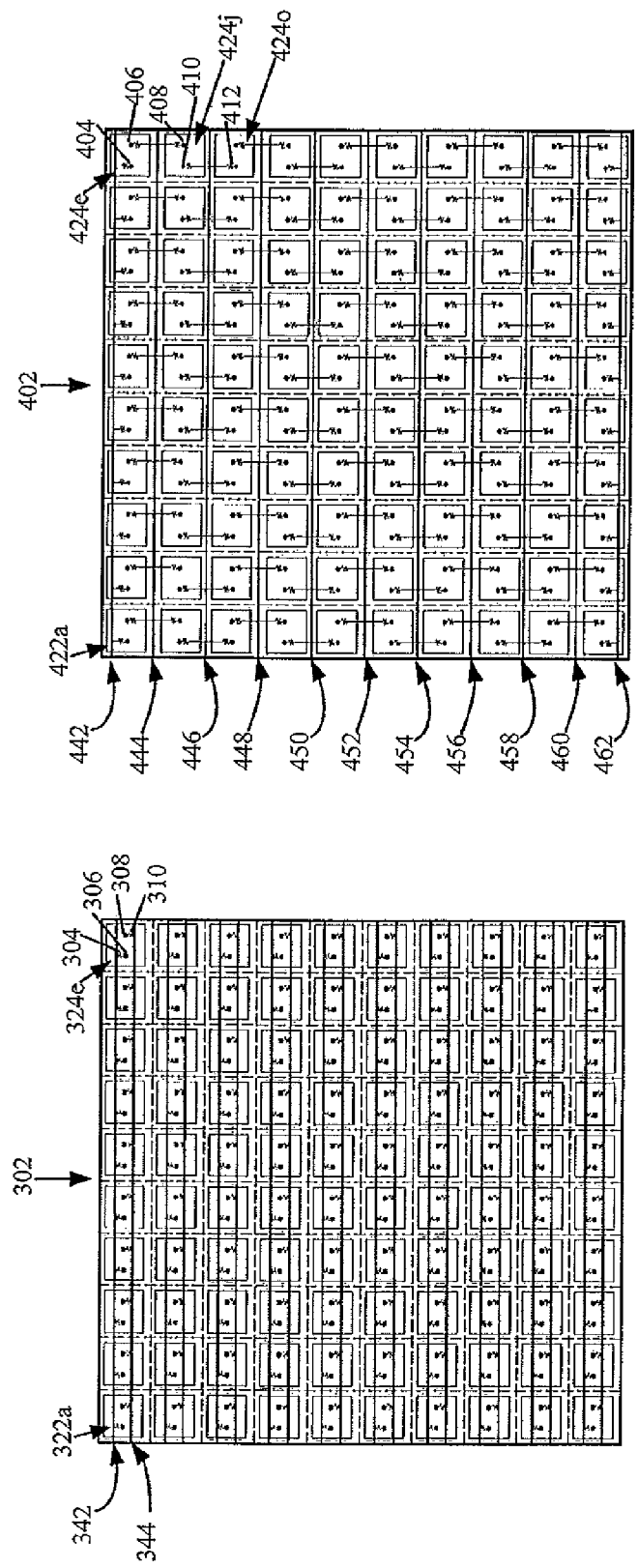
FIG. 2a is a side view of a sub-millimeter 10×10 APD array configured with an independent bias circuit, in one embodiment of the present invention.
FIG. 2b is a side view of a sub-millimeter 10×10 APD array configured with a common bias circuit, of the present invention.

The APD photo sensor array 120 incorporated into block detector 100 comprising the present invention is a monolithic or assembled array of sub-millimeter APDs. A top view of embodiments of the APD photo sensor array 120 illustrated in FIGS. 1A and 1B is illustrated in FIGS. 2A and 2B. In the embodiments illustrated, a ten by ten array of APD photo sensors or a five by five array of APD photo sensors are shown. It is to be understood that the specific array of APD photo sensors illustrated in FIGS. 1B, 2A and 2B are for illustrative purposes only and are not intended to limit the scope of the present invention. The dimensions of an array of APD photo sensors may be any n×n array configuration assembled in accordance with the present invention. Generally, the dimensions of the APD photo sensor array may be determined by the size of the scintillator crystal and the overall desired size of the detector. In one embodiment, it is contemplated that the each APD photo sensor cell in the array of APD photo sensors 320, 420 shall be approximately 1.0 millimeters (mm) per side or less (each cell has an area of <1.0 mm×<1.0 mm) and each APD photo sensor cell operates independently. In some embodiments, each APD photo sensor cell in the array of APD photo sensors 320, 420 may have an area of <0.05-1.0 mm×<0.05-1.0 mm. As illustrated in the embodiments, shown in FIGS. 2A and 2B, each APD photo sensor cell in the array of APD photo sensors 302, 402 is connected to a common bias circuit to facilitate high voltage bias and signal readout. The common bias provides for easier integration and a higher fill factor. Although it is not shown in the Figures, it is contemplated that in another embodiment, each APD photo sensor cell in the array of APD photo sensors 320 may have an independent bias circuit.

Of the two embodiments illustrated in FIGS. 2A and 2B, the embodiment illustrated in FIG. 2B is preferred, as the embodiment illustrated in FIG. 2A is more difficult and costly to manufacture. A problem with the design illustrated in FIG. 2A is the high and low voltage lines 312 and 314 are too close. Electrical lines, such as lines 312 and 314, configured on standard printed circuit board material that are in such close proximity cannot function properly. Since there will be a substantial difference between the high and low voltage lines 312 and 316, arcing will occur between the high and low voltage lines, unless the base material, of which the array of APD photo sensors is comprised, is a material such as ceramic or Teflon. Accordingly, using an inexpensive base material such as FR4 to create the array of APD photo sensors is not feasible because the physical properties of the base material cannot support voltage lines of varying voltage being in close proximity. However, the problem resulting from having two voltage lines in close proximity on a chip may be overcome when a design, such as that illustrated in FIG. 2A, is manufactured using a base material such as Teflon or ceramic. While it is contemplated that an embodiment of the invention can be manufactured in accordance with design set forth in FIG. 2A, manufacturing such a design adds substantial expense to the process when base materials such as ceramic and Teflon are used.

An alternative embodiment, illustrated in FIG. 2B allows for the use of inexpensive underlying base material, such as FR4 by eliminating the arcing problem through increasing the distance between the high voltage lines 442, 446, 450, 454, 458, 462 and the low voltage lines 444, 448, 452, 456, 460. As illustrated in FIG. 2B, this is accomplished by having the anode and cathodes of two adjacent APDs in APD photo sensor cells within an array share high and low voltage lines. As shown, APD cell 424e is connected to high voltage line 442 through connection 404. APD cells 424e and 424j are both connected to low voltage line 444 through connections 406 and 408, and APD cells 424j and 424o are both connected to high voltage line 446 through connections 410 and 412. It is to be understood that whether the anode or cathode of an APD is an APD cell, in the present invention, connected to high or low voltage is irrelevant. The important point is to have a voltage difference between the anode and cathode of the APD. In one embodiment, the anode may be connected to ground and the cathode connected to a positive high voltage. In an alternative embodiment, the cathode may be connected to ground and the anode connected to a negative high voltage.

Referring to FIG. 3, this figure presents an illustration of a schematic drawing of an example of the common biasing circuit and the signal output connection of an array of APD photo sensors 140 comprised of ten APD photo sensor cells 142a-142j. This illustration is a more detailed schematic of a portion of the array of APD photo sensor array 302 illustrated in FIG. 2B. As illustrated, the array of APD photo sensors 140 illustrated comprises a five by two array of APD photo sensor cells 140. As illustrated, each of the ten APD photo sensor cells 142a-142j are comprised of the same components and circuitry and are connected to ground and a common high voltage line in the same manner. Accordingly, of the ten APD photo sensor cells 142a-142j, cell 142a will be explained to illustrate operation of each APD photo sensor cell in array 140. The input of APD photo sensor cell 142a is connected to high voltage line 144, wherein the cathode of the APD 150a is connected to the high voltage line 144 through resistor 146a. The cathode of APD 150a is also connected to a capacitor 148a and ground 158a. The anode of APD 150a is connected to ground 158a through resistor 152a and the output of the APD cell 142a to the ASIC (not shown) through a bump-bond connection 156a through capacitor 154a. The high voltage capacitor 148a is used to decouple noise from the high voltage line; the regular low voltage capacitor 154a is AC-coupling the APD signal to subsequent signal chain. Capacitor 154a can be eliminated if the DC-coupling signal path is desired. Node 156a D11, subsequence CFA, capacitor 156a, and ground plane 158a also form a low-impedance current loop for signal high frequency components, facilitating event timing detection.

FIGS. 4A and 4B are side views of two embodiments of package configurations of the sub-millimeter APD photo sensor arrays 160 and 170 and the respective front-end APD-ASIC 166 and 176 connected through bump-bond connections 168 and 178. As illustrated in FIG. 4B, the embodiment shown also includes a printed circuit board sandwiched between the APD photo sensor array 170 and the front end APD-ASIC 176, allowing the size of the APD-ASIC 176 to be substantially reduced.

Figure 5:
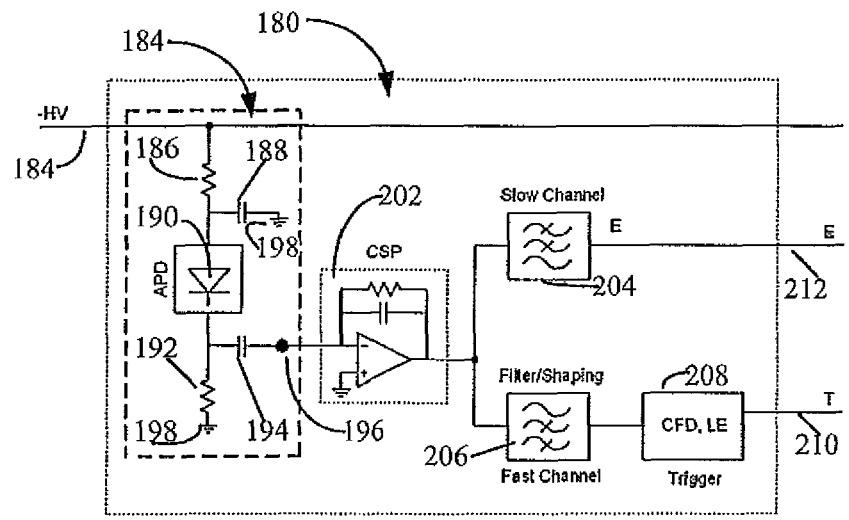
FIG. 5 is an embodiment of a schematic block diagram of a single APD readout circuit from the bias circuit to the energy and timing outputs of the APD ASIC.

When light enters a photo sensor, it is desirable to know two pieces of information, when the photon is received by the photo sensor (timing) and how large the signal received is (amount of energy or the number of photons received at a given instance in time). This configuration facilitates the ability to determine the timing at which photons are received and the number of photons received by facilitating the ability to determine the amount of energy received by each APD at an instance in time, thereby making the embodiment linear. FIG. 5 illustrates the circuitry within the APD cell 184 and the APD ASIC 180 utilized to determine the timing and energy information necessary in PET imaging applications. As illustrated, a sub-millimeter APD cell 184 having its output 196 connected to a charge sensitive pre-amplifier (CSP) 202, is positioned on the APD ASIC 180. The CSP 202 facilitates the collection of the charges from the APD 190. Next the CSP 202 output signal is split into to channels, a slow channel 204 and fast channel 206. The signal output by the CSP 202 has a high frequency and a low frequency component. The fast channel 206, which receives the signal output by the CSP 202, is performing filtering or shaping of the signal received to emphasize the high frequency components. The output of the fast channel 206 is received by a trigger 208, and a constant fraction discriminator (CFD) or a leading edge (LE) trigger 210. The slow channel 204, which receives the signal output by the CSP 202, is performing filtering or shaping of the signal received to emphasize the low frequency components. The output from slow channel 204 is representative of the energy received by the APD cell 184 and is proportional to the number of photons received by the APD cell 184.

Figure 6:
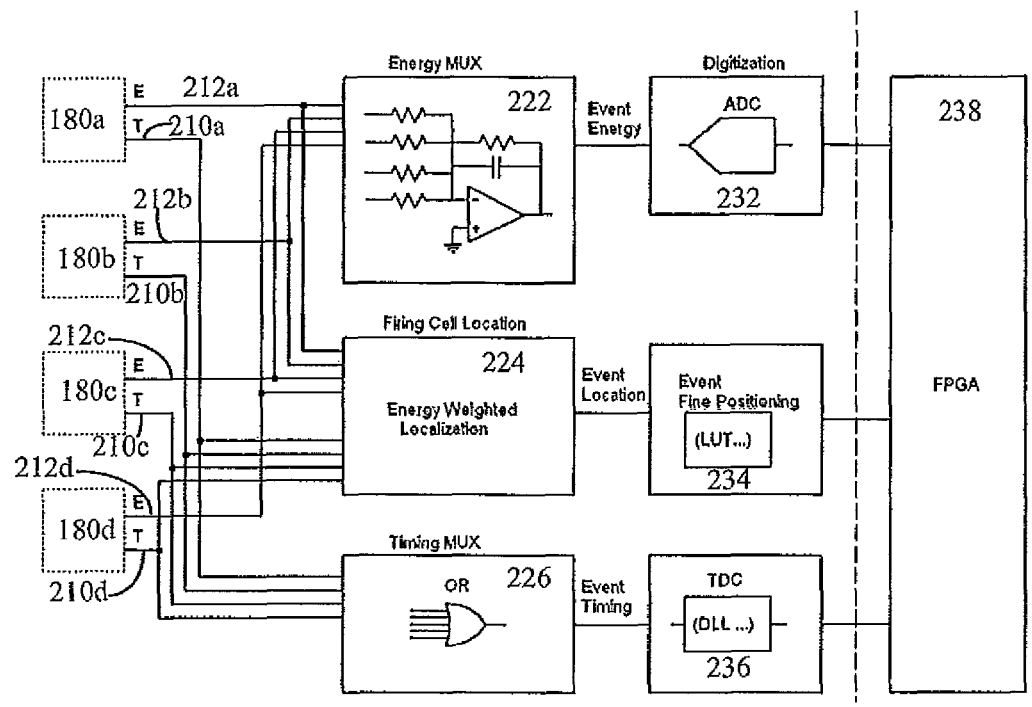
FIG. 6 is an illustration of an embodiment of back-end circuitry within the APD ASIC or system processing electronics of the present invention that may be utilized to determine energy, position and timing of each PET event.

FIG. 6 is an illustration of the circuitry within the APD ASIC, including the circuitry from FIG. 5 at 180*a*-180*d*, where stages of sub-millimeter APD cells, each are connected to CSPs positioned on the APD ASIC and connected to a slow channel and a fast channel that provide energy outputs 212*a*-212*d* and timing outputs 210*a*-210*d*. Each energy output 212*a*-212*d* is received by an energy multiplexer 222 and a cell location 224 unit (a look up table). Each timing output is received by a timing multiplexer 226. The output of the timing multiplexer 226 is received by a timing digital convertor 236. The output of the energy multiplexer 222 is received by an analog to digital convertor 232. The output of the cell location is received by the look up table 234 to perform event fine positioning. All signals exiting the analog to digital convertor 232, the look up table 234 and the timing digital convertor have been digitized and are then processed by the processor 238 which is a commercially available chip on the market. It is contemplated, as illustrated in FIG. 6, that the circuitry shown, other than the APD Cell and the processor, is on the APD ASIC. However, it is to be understood that it is contemplated that the circuitry illustrated in FIG. 6 is not required to be implemented through the APD ASIC and may be implemented in various embodiments on other printed circuit boards.

The above specification, examples and data provide a description of the manufacture and use of the invention. Since many embodiments of the invention can be made without departing from the spirit and scope of the invention, the invention resides in the claims hereinafter appended.

What is claimed is:

1. A photodetector comprising:
   at least one scintillator and at least one photosensor positioned proximate to the at least one scintillator,
   wherein the at least one photosensor has a surface area substantially equal to a surface area of a face of the at least one scintillator,
   wherein the photosensor is comprised of a plurality of avalanche photodiodes cells arranged in an n×n array,
   wherein n>1, and wherein each avalanche photodiode cell has a surface area that is not greater than one square millimeter and a separate output for an avalanche photodiode positioned thereon,
   wherein the at least one photosensor is configured to facilitate reading of the output of the avalanche photodiode on the cell, and
   wherein two adjacent avalanche photodiodes in a same column within the photosensor share a first common voltage line and do not share a second common voltage line.

2. The photodetector of claim 1 wherein the dimensions of each avalanche photodiode cell has four sides ranging between 0.05 mm-1.0 mm.

3. The photodetector of claim 1 wherein the at least one scintillator comprises an array of scintillator crystals wherein each of the scintillator crystals in the array has a photosensor positioned proximate thereto.

4. The photodetector of claim 1 wherein each avalanche photodiode in the array of cells is electrically connected to at least one common bias circuit.

5. The photodetector of claim 1 wherein each of the avalanche photodiodes within the photosensor is electrically connected to an independent bias circuit.

6. The photodetector of claim 1 wherein two adjacent avalanche photodiodes within the photosensor are connected so that anodes of the two adjacent avalanche photodiodes share the first common voltage line and cathodes of the two adjacent avalanche photodiodes share the second common voltage line.

7. The photodetector of claim 6 wherein a first avalanche photodiode of the two adjacent avalanche photodiodes is in a first row and a second avalanche photodiode of the two adjacent avalanche photodiodes is in a second row.

8. The photodetector of claim 6 wherein a first avalanche photodiode of the two adjacent avalanche photodiodes is in a first column and a second avalanche photodiode of the two adjacent avalanche photodiodes is in a second column.

9. The photodetector of claim 1 including an application specific integrated circuit configured in a manner to facilitate reading of the output from each avalanche photodiode in the array.

10. The photodetector of claim 9 wherein the application specific integrated circuit includes a plurality of sensing circuits connected in a manner to facilitate reading of the output of each of the avalanche photodiodes in the array,
   wherein each sensing circuit generates, in response to an avalanche photodiode cell output signal received, signals representative of energy, position and timing of each PET event.

11. The photodetector of claim 9 further including a printed circuit board, sandwiched between and electrically connected to the application specific integrated circuit and the photodiode array,
   wherein the printed circuit board is configured in a manner to facilitate transmission of the output from each avalanche photodiode in the array to the application specific integrated circuit.

12. The photodetector of claim 11 wherein the surface area of the printed circuit board is sized substantially equivalent to the surface area of a face of the photosensor and the surface area of a face of the application specific integrated circuit is substantially smaller.

13. The photodetector of claim 1 wherein the at least one scintillator comprises an array of scintillator crystals wherein each of the scintillator crystals in the array has a photosensor array positioned proximate thereto.

14. A photodetector comprising:
   at least one scintillator and a photodiode array positioned proximate to at least one scintillator, wherein the photodiode array has a surface area substantially equal to a surface area of a face of the scintillator, wherein the photodiode array is comprised of a plurality of avalanche photodiodes arranged in an array, wherein each avalanche photodiode in the array is positioned on a cell having a surface area that is not greater than one square millimeter, wherein each avalanche photodiode in the array has a separate output to facilitate a readout of each avalanche photodiode separately, and wherein two adjacent avalanche photodiodes in a same column within the photodiode array share a first common voltage line and do not share a second common voltage line.

15. The photodetector of claim 14 wherein the output of each avalanche photodiode is received by one of a plurality of a sensing circuits, wherein each sensing circuit generates, in response to the signal received, output signals representative of energy, position and timing of each PET event.

16. The photodetector of claim 14 wherein each of the avalanche photodiodes within the photosensor are connected to a shared high voltage line.

17. The photodetector of claim 14 wherein two adjacent avalanche photodiodes within the photosensor are connected so that anodes of the two adjacent avalanche photodiodes share the first common voltage line and cathodes of the two adjacent avalanche photodiodes share the second common voltage line.

18. The photodetector of claim 14 further comprising:

an application specific integrated circuit configured to facilitate reading the output from each avalanche photodiode in the array, wherein the application specific integrated circuit includes:
   a plurality of sensing circuits connected to facilitate reading the output of each of the avalanche photodiodes in the array,
   wherein each sensing circuit generates, in response to an output signal received from an avalanche photodiode, signals representative of energy, position and timing of each PET event.

19. The photodetector of claim 14 wherein the dimensions of each cell has four sides ranging between 0.05 mm-1.0 mm.

20. A method in a plurality of photodetector cells a photo sensor wherein each cell includes an avalanche photo diode and wherein each photodetector cell has a surface area that is not greater than one square millimeter, in which the method comprises:

reading an output signal from each avalanche photodiode;

processing each output signal from each of the avalanche photodiodes to determine energy, position and timing of each PET event, and wherein two adjacent avalanche photodiodes in a same column within the plurality of photodetector cells share a first common voltage line and do not share a second common voltage line.

\* \* \* \* \*